(12) United States Patent
Sakaguchi et al.

(10) Patent No.: US 9,795,352 B2
(45) Date of Patent: Oct. 24, 2017

(54) IMAGE PROCESSING APPARATUS AND X-RAY DIAGNOSTIC APPARATUS

(75) Inventors: Takuya Sakaguchi, Shioya-Gun (JP); Takashi Ichihara, Nagoya (JP); Masanori Matsumoto, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 846 days.

(21) Appl. No.: 12/688,255

(22) Filed: Jan. 15, 2010

(65) Prior Publication Data

US 2010/0183207 A1    Jul. 22, 2010

(30) Foreign Application Priority Data

Jan. 22, 2009    (JP) ................................. 2009-012119

(51) Int. Cl.
*G06T 7/00*    (2017.01)
*A61B 6/00*    (2006.01)

(52) U.S. Cl.
CPC ............. *A61B 6/504* (2013.01); *A61B 6/481* (2013.01); *A61B 6/507* (2013.01); *A61B 6/4441* (2013.01)

(58) Field of Classification Search
USPC ........................................................ 382/132
See application file for complete search history.

(56) References Cited

U.S. PATENT DOCUMENTS

| 7,496,175 B2 | 2/2009 | Sakaguchi et al. |
| 2003/0108149 A1* | 6/2003 | Tsuyuki ................. A61B 6/032 378/54 |
| 2007/0098134 A1* | 5/2007 | Toyoshima et al. .............. 378/4 |

(Continued)

FOREIGN PATENT DOCUMENTS

| CN | 1957848 A | 5/2007 |
| JP | 2004-141245 A | 5/2004 |

(Continued)

OTHER PUBLICATIONS

Gibson et al., TIMI Frame Count, A Quantative Method of Assessing Coronary Artery Flow, Circulation, 1996;93, pp. 879-888, 1996.

(Continued)

*Primary Examiner* — Eliza Lam
(74) *Attorney, Agent, or Firm* — Kenichiro Yoshida (57) ABSTRACT

An image processing apparatus includes a storage unit which stores data of X-ray projection images generated through a angiographic imaging sequence, a generation unit which, based on the data, generates a reference time density curve concerning a reference region which is set as a blood supply region, and time density curves concerning perfusion regions which are set as a blood supplied region, a measurement unit which measures delay times for which a contrast medium reaches the perfusion regions from the reference region, from relationships between the reference time density curve and the time density curves, a calculation unit which calculates, respectively for the perfusion regions, first indices expressing correlations of the time density curves to the reference time density curve within a period determined on the basis of the delay times, and a first image generation unit which generates a first image expressing spatial distribution of the first indices.

6 Claims, 11 Drawing Sheets

(56) References Cited

U.S. PATENT DOCUMENTS

| | | | |
|---|---|---|---|
| 2008/0107233 A1* | 5/2008 | Sakaguchi et al. | 378/91 |
| 2009/0306505 A1* | 12/2009 | Yoshikawa et al. | 600/443 |
| 2010/0030081 A1* | 2/2010 | Masuzawa et al. | 600/459 |
| 2010/0049413 A1* | 2/2010 | Makino et al. | 701/65 |

FOREIGN PATENT DOCUMENTS

| | | |
|---|---|---|
| JP | 2005-95340 A | 4/2005 |
| JP | 2005-137558 A | 6/2005 |
| JP | 2005-237825 A | 9/2005 |
| JP | 2006-153867 A | 6/2006 |
| JP | 2007-144139 A | 6/2007 |
| JP | 2007-283103 A | 11/2007 |
| JP | 2008-136800 A | 6/2008 |

OTHER PUBLICATIONS

CN Office Action for corresponding CN Application No. 201010106662.9 mailed on Jul. 20, 2011.

Jerosch-Herold, Michael et al, Time delay for arrival of MR contrast agent in collateral-dependent myocardium, IEEE Transactions on Medical Imaging, vol. 23 No. 7, 2004, pp. 881-890.

Japanese Office Action with English Translation for Japanese Patent Application No. 2009-012119 mailed on Apr. 2, 2013.

* cited by examiner

IMAGE PROCESSING APPARATUS AND X-RAY DIAGNOSTIC APPARATUS

CROSS-REFERENCE TO RELATED APPLICATIONS

This application is based upon and claims the benefit of priority from prior Japanese Patent Application No. 2009-012119, filed Jan. 22, 2009, the entire contents of which are incorporated herein by reference.

BACKGROUND OF THE INVENTION

1. Field of the Invention

The present invention relates to an image processing apparatus and an X-ray diagnostic apparatus for imaging perfusion in myocardium.

2. Description of the Related Art

For example, blood supply to (or perfusion of blood in) myocardium is indispensable for a heart to beat. In conventional angiographic diagnoses, only blood vessels are observed while myocardium is not often observed. Owing to recent progress in imaging technology, X-ray images have become able to be obtained with high time resolution and with high image quality, and concrete methods for measuring myocardial perfusion have hence been proposed. For example, Jpn. Pat. Appln. KOKAI Publication No. 2008-136800 has proposed a method for creating a perfusion image from a relationship between a reference time density curve, which concerns a reference region set as a blood supply region for myocardium, and time density curves, which concern plural local region set in a myocardial region.

Consideration will now be taken into a case that a constricting lesion exists in a blood vessel. Since the constricting lesion hinders blood flow, periphery of the blood vessel where a stenosis occurs requires a longer time until a contrast medium reaches, or a sufficient amount of blood is not supplied, in comparison with a case of no stricture occurring. For example, a first peripheral region of a first stenosis is supposed to be supplied with a sufficient amount of blood after a long time. A second peripheral region of a second stenosis is supposed to be supplied with an insufficient amount of blood after a long time. In this case, a time density curve at the first region has a similar shape and a different time phase to those of a time density curve (TDC) at a normal region. However, a time density curve at the second region has a different shape and a different time phase to those at a normal region. Therefore, perfusion images indicative of risk are obtained from both regions. Consequently, there is a problem that whether or not blood is supplied to myocardium in these regions cannot be distinguished although blood can be found to not be supplied at adequate timing to myocardium in the regions.

BRIEF SUMMARY OF THE INVENTION

The present invention has been made in view of the above circumstances and has an object of providing an image processing apparatus and an X-ray diagnostic apparatus which allow perfusion to be observed properly at a target portion.

According to an aspect of the present invention, it is provided that an image processing apparatus including: a storage unit which stores data of a plurality of X-ray projection images generated through a angiographic imaging sequence; a generation unit which, based on the data of the plurality of X-ray projection images, generates a reference time density curve concerning a reference region which is set as a blood supply region for a target portion, and a plurality of time density curves concerning a plurality of perfusion regions which are set as a blood supplied region in the target portion; a measurement unit which measures a plurality of delay times for which a contrast medium reaches the plurality of perfusion regions from the reference region, from relationships between the reference time density curve and the plurality of time density curves; a calculation unit which calculates, respectively for the plurality of perfusion regions, a plurality of first indices expressing correlations of the plurality of time density curves to the reference time density curve within a period determined on the basis of the delay times; and a first image generation unit which generates a first image expressing spatial distribution of the plurality of first indices.

According to another aspect of the present invention, it is provided that an X-ray diagnostic apparatus including: an X-ray tube which generates an X-ray; an X-ray detector which detects the X-ray which penetrates a subject; a storage unit which stores data of a plurality of X-ray projection images generated through a angiographic imaging sequence by the X-ray detector; a generation unit which, based on the data of the plurality of X-ray projection images, generates a reference time density curve concerning a reference region which is set as a blood supply region for a target portion, and a plurality of time density curves concerning a plurality of perfusion regions which are set as a blood supplied region in the target portion; a measurement unit which measures a plurality of delay times for which a contrast medium reaches the plurality of perfusion regions from the reference region, from relationships between the reference time density curve and the plurality of time density curves; a calculation unit which calculates, respectively for the perfusion regions, a plurality of first indices expressing correlations of the plurality of time density curves to the reference time density curve within a period determined on the basis of the delay times; and a first image generation unit which generates a first image expressing spatial distribution of the plurality of first indices.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Hereinafter, an embodiment of the invention will be described in details below. In the embodiment below, an image processing apparatus according to the invention will be described to be incorporated in an X-ray diagnostic apparatus.

Figure 1:
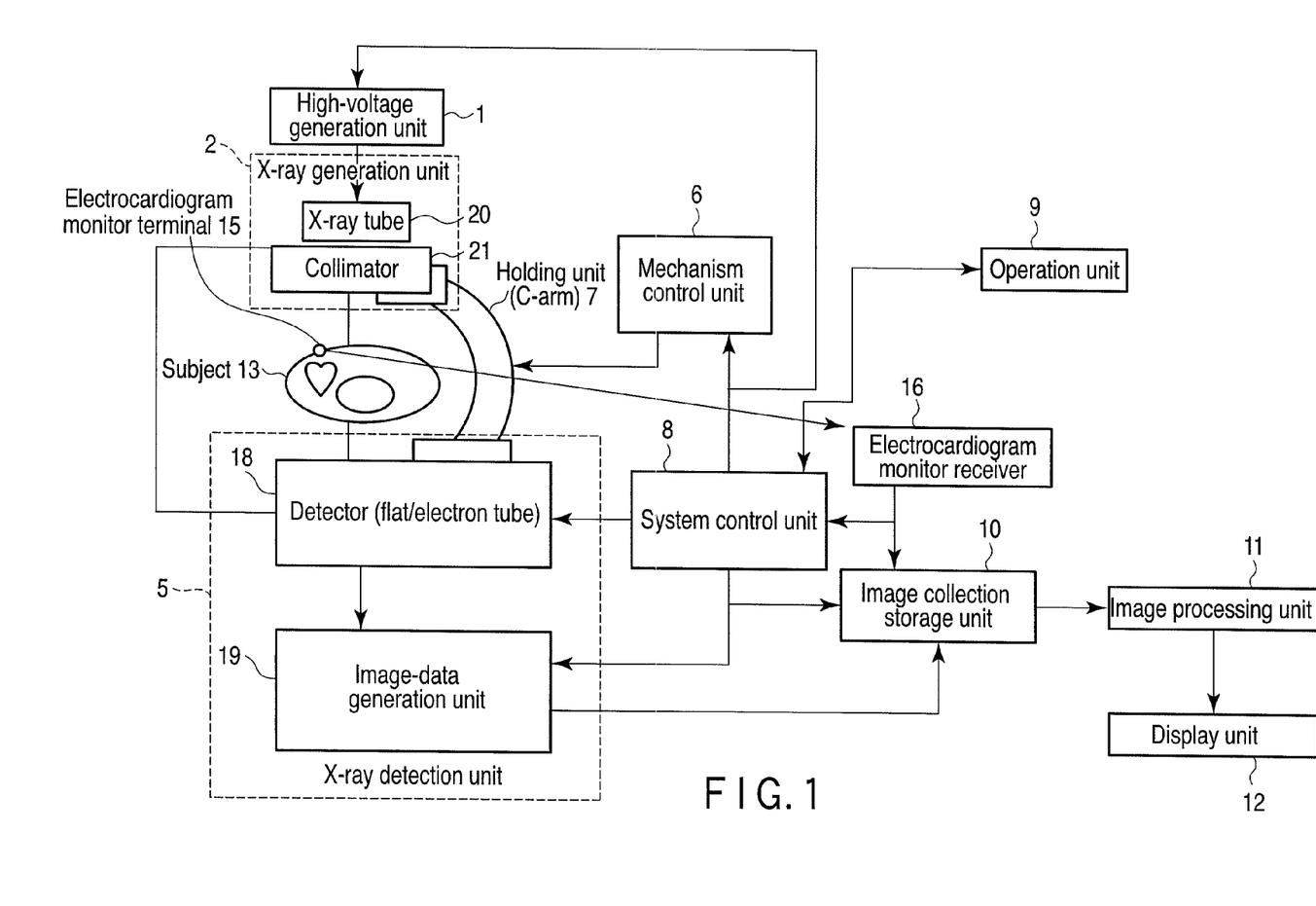
FIG. 1 is a diagram representing an embodiment of an X-ray diagnostic apparatus comprising an image processing apparatus according to the invention.

FIG. 1 represents a configuration of an X-ray diagnostic apparatus according to the present embodiment. The X-ray diagnostic apparatus includes a C-arm 7. The C-arm 7 is rotatably supported by a mechanism control unit 6. An X-ray generation unit 2 is attached to an end of the C-arm 7. The X-ray generation unit 2 includes an X-ray tube 20 and an collimator 21. A high-voltage generation unit 1 generates a high voltage (tube voltage) to be applied between electrodes of the X-ray tube 20, and also generates a filament current to be supplied to a filament of the X-ray tube 20. Under control of a system control unit 8, a high-voltage control unit 17 controls the tube voltage and/or filament current generated by the high-voltage generation unit 1.

An X-ray detection unit 5 is attached to another end of the C-arm 7. The X-ray detection unit 5 includes a detector 18 and an image data generation unit 19 which processes an output of the detector 18 thereby to generate image data. The detector 18 faces the X-ray tube 20 through a subject 3 located therebetween, who is laid on a bed. The detector 18 is typically a solid flat detector constituted by two-dimensionally arraying plural detection elements (pixels) which directly or indirectly convert an incident X-ray into electrical charges. Under control of the system control unit 8, the X-ray detection unit 5 repeats, in a constant cycle, one cycle of detection operation which consists of charging, reading, and resetting of electrical charges. An electrocardiogram monitor terminal 15 is set on the subject 3. The electrocardiogram monitor receiver unit 16 receives a signal from the electrocardiogram monitor terminal 15, and generates electrocardiogram data of the subject 3. An operation unit 9 is connected to the system control unit 8.

The operation unit 9 is provided to transmit various instructions from a user to the system control unit 8, and includes various input devices such as a keyboard and a mouse. A display unit 12 is constituted by a cathode-ray tube (CRT), a liquid crystal display (LCD), and so on.

The image data generation unit 19 sequentially generates X-ray images expressing a subject subjected to angiography. For example, the generated X-ray images constitute a video including ten to thirty images per second, which continues 3 to 60 seconds. An image collection storage unit 10 stores image data collected from the image data generation unit 19, with the image data associated with cardiac phase data.

Figure 2:
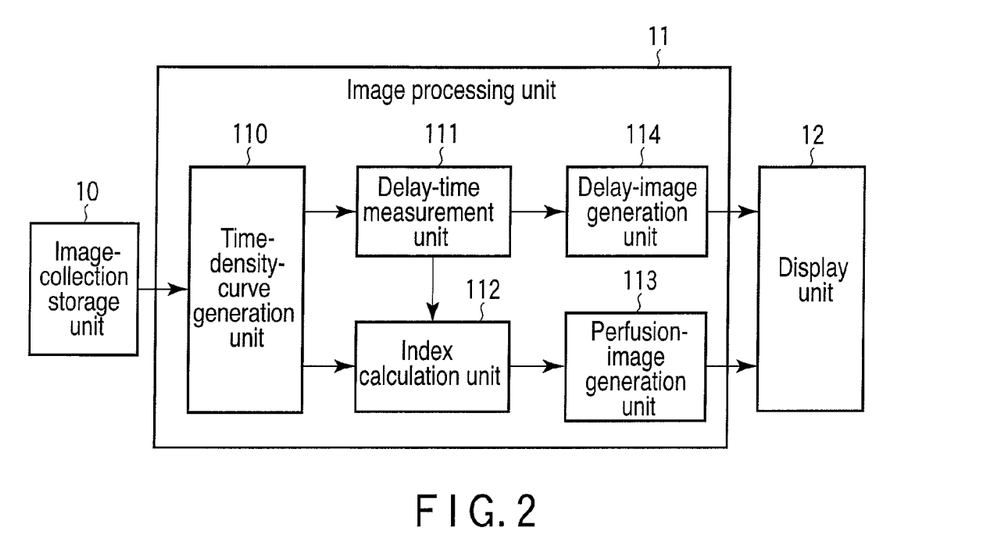
FIG. 2 is a functional block diagram of an image processing unit.

FIG. 2 represents functional blocks of an image processing unit 11. The image processing unit 11 includes a time-density-curve generation unit 110, a delay-time measurement unit 111, an index calculation unit 112, a perfusion-image generation unit 113, and a delay-image generation unit 114.

Based on data of plural images generated through a cardiac coronary angiographic imaging sequence, the time density curve (TDC) generation unit 110 generates a reference time density curve concerning a reference region set as a blood supply region for myocardium, and plural time density curves concerning plural local regions (perfusion regions) set in a myocardial region.

From the relation between time density curve and the plural time density curves, the delay-time measurement unit 111 measures plural delay times which are caused until the contrast medium reaches the plural perfusion regions from the reference region.

The index calculation unit 112 calculates plural indices (perfusion values) expressing correlations of time density curves to the reference time density curve in periods after elapse of the delay times, respectively for the perfusion regions.

The perfusion-image generation unit 113 generates a perfusion image (first image) expressing spatial distribution of the perfusion values obtained as described above. The delay-image generation unit 114 generates a delay image (second image) expressing spatial distribution of the delay times measured as described above. The display unit 12 displays the perfusion image and the delay image compared with each other on a screen.

Figure 3:
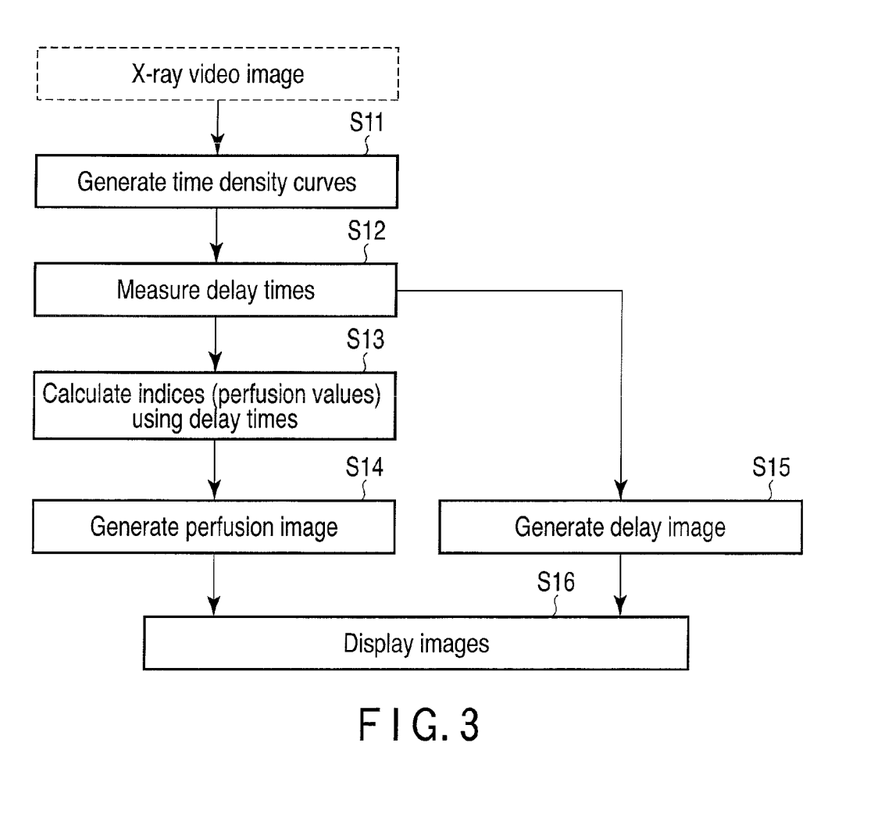
FIG. 3 is a flowchart representing a processing procedure of the image processing unit.

FIG. 3 is a flowchart representing an example of a processing procedure of the image processing unit 11. Contents of processings in respective steps will now be described below.

[Time-Density-Curve Generation: Step S11]

Figure 4A:
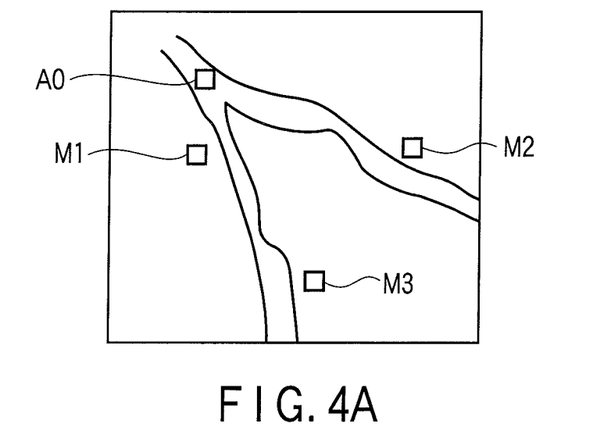
FIGS. 4A and 4B are to graphically describe a generation processing for generating time density curves.
Figure 4B:
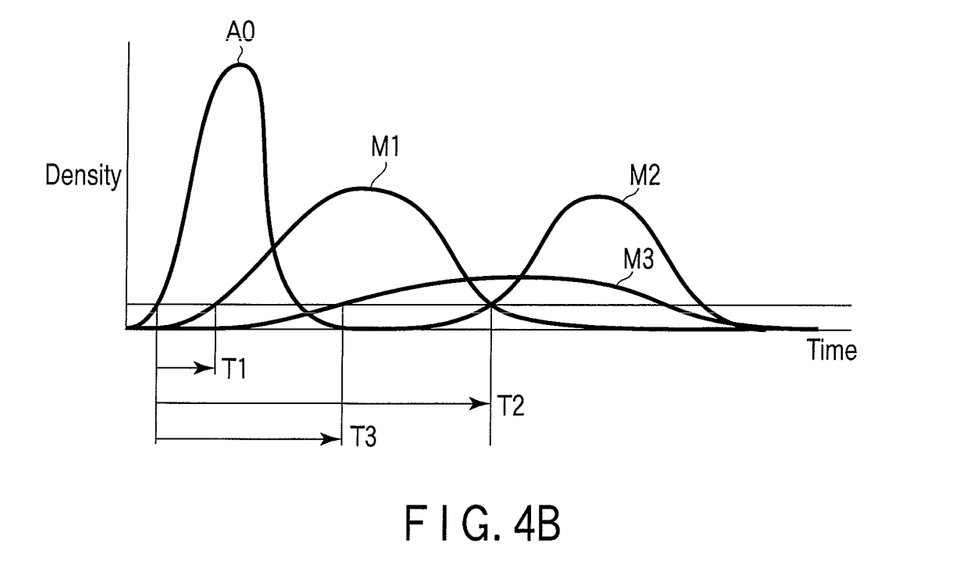

Based on data of plural images generated through the cardiac coronary angiographic imaging sequence, the time-density-curve generation unit 110 generates a reference time density curve concerning a reference region set as a blood supply region for myocardium, and plural time density curves concerning plural local regions set in a myocardial region. A time density curve is a characteristic curve drawn by plotting times (frame numbers of images) along the horizontal axis as well as densities (brightness) of images along the vertical axis, and can be obtained for each pixel. For example, where A0 is a reference region and myocardium M1, M2, and M3 are perfusion regions as represented in FIG. 4A, time density curves as represented in FIG. 4B are obtained.

[Delay Time Measurement: Step S12]

The delay image measurement unit 111 measures delay times for plural time density curves relative to a time density curve at the reference region. That is, in FIG. 4B, time differences T1, T2, and T3 of time density curves at the myocardium M1, M2, and M3 from the time density curve at A0 are measured as delay times at the myocardium M1, M2, and M3, respectively. For example, delay times are calculated by reading time points when slopes of the respective time density curves are maximized.

[Perfusion Value Calculation: Step S13]

For the perfusion regions, respectively, the index calculation unit 112 calculates plural indices (perfusion values) expressing correlations of time density curves after elapse of the delay times, relative to the reference time density curve. For example, in case of employing a method such as Patlak Plot disclosed in a known publication, a perfusion value $K_1$ is calculated based on a flow model of a contrast medium flowing into/out of myocardium, which is defined by an expression as follow. Ca(t) corresponds to the reference time density curve at the reference region A0, and Cmyo(t) corresponds to the curves at the myocardium M1, M2, and M3.

$$\frac{dC_{myo}(t)}{dt} \cong K_1 C_a(t)$$

Integrating the above formula provides:

$$C_{myo}(t) = K_1 \times \int_0^T C_a(t) dt + p$$

When y axis represents $C_{myo}(t)$ and x axis represents $\int_0^T C_a(t)dt$ to plot a line on a graph, a straight slope of the line gives $K_1$.

Figure 5A:
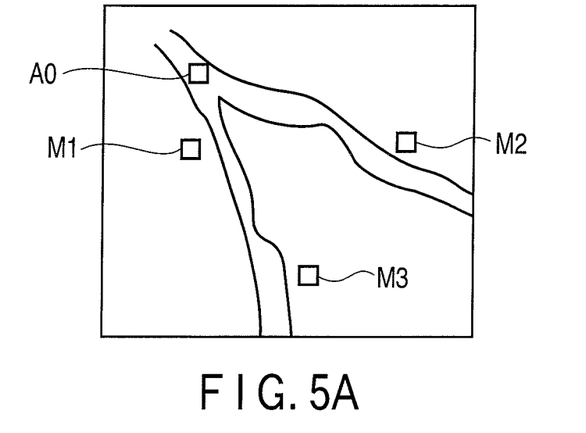
FIGS. 5A and 5B are to graphically describe a calculation processing for calculating perfusion values.
Figure 5B:
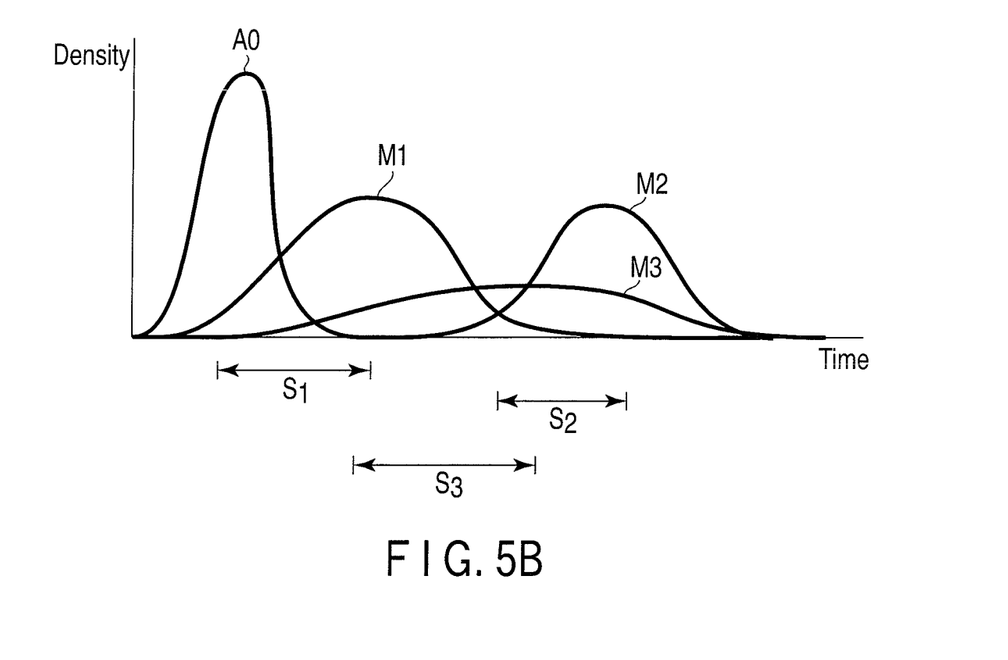
Figure 6:
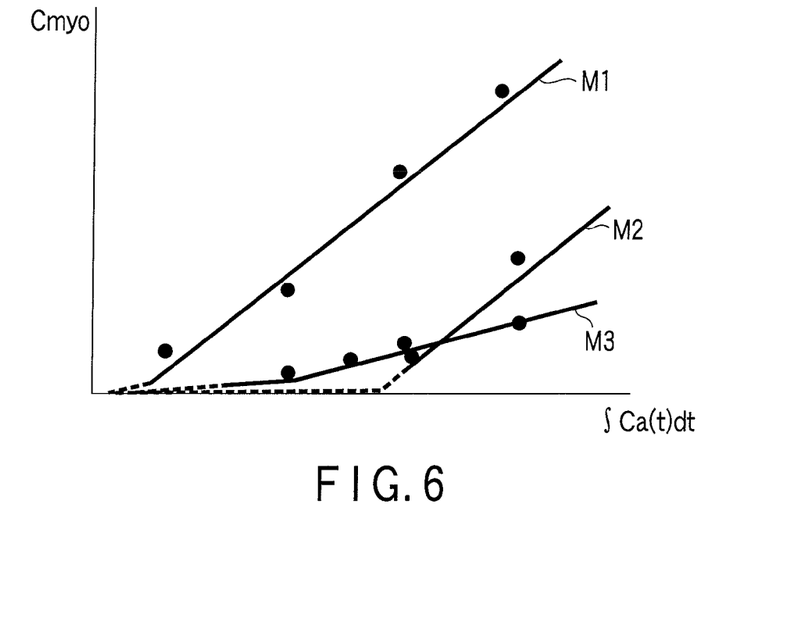
FIG. 6 represents an example of Patlak Plot.

The index calculation unit 112, for example in FIG. 5A and FIG. 5B, performs a model calculation on the basis of data of a section S1 with respect to the myocardium M1 as well as on the basis of data of a section S2 with respect to the myocardium M2. In this manner, slopes are substantially equal between regions where time density curves are simply delayed, as represented in FIG. 6, and accordingly, equal perfusion values are calculated out. In FIG. 6, an slope is apparently small at the myocardium M3, and a region like this can be determined to be an abnormal region.

[Perfusion Image Generation: Step S14]

The perfusion-image generation unit 113 generates an image (perfusion image) expressing spatial distribution of perfusion values obtained through the step S13.

[Delay Image Generation: Step S15]

Figure 7:
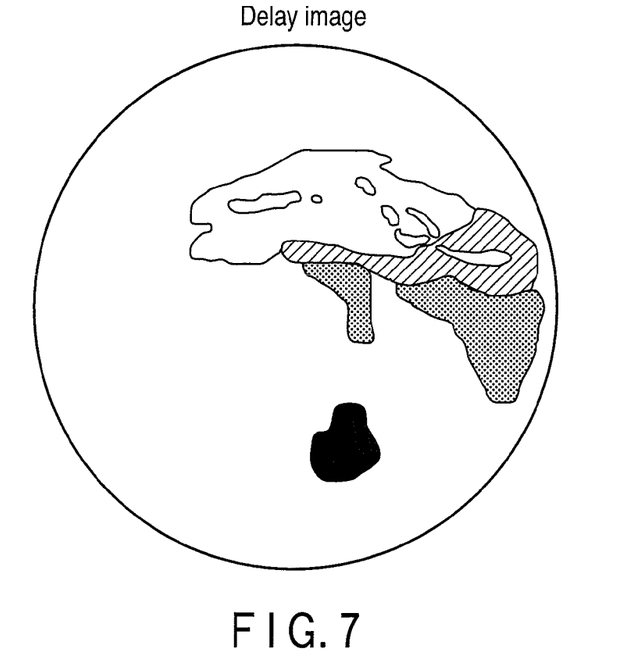
FIG. 7 represents an example of a delay image.

The delay-image generation unit 114 generates an image (delay image) which expresses spatial distribution of the delay times measured in the step S12. For example, the delay image are displayed as an image as represented in FIG. 7. In FIG. 7, delay times are respectively expressed by concentrations of cross-hatches. Alternatively, delay times may be displayed as a color image.

[Image Display: Step S16]

Figure 8:
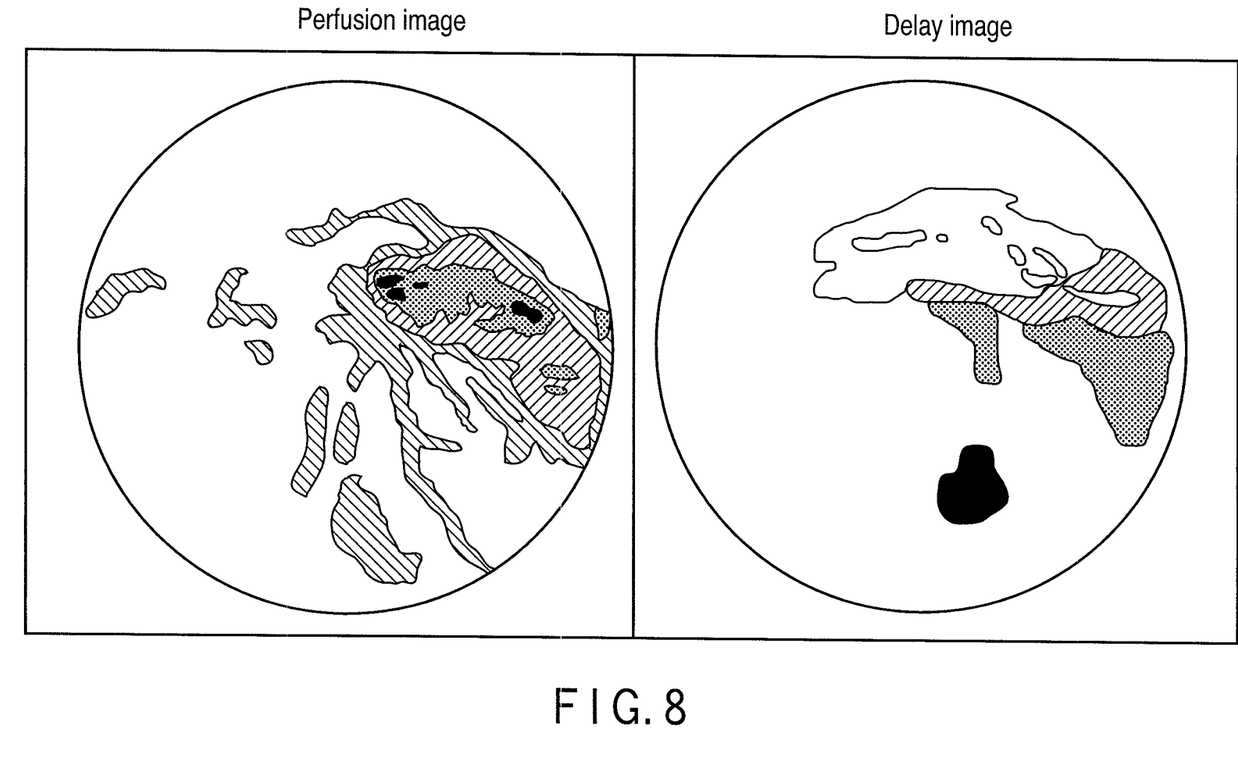
FIG. 8 represents an example of displayed images.

The display unit 12 displays a perfusion image and a delay image, comparing both images. For example, as represented in FIG. 8, a perfusion image and a delay image are respectively displayed on the left and right sides of the monitor. In this example, the images viewed from equal angles are displayed in equal sizes. The forgoing term of "comparing" is intended to mean a display method in which not only images are simply arrayed in a row but also, for example, mouse pointers may simultaneously move on the two images at equal coordinates, or magnification rates of two images may be changed to be constantly equal to each other. Alternatively, one of the two images may be expressed by colors, and the other one may be expressed by brightness. For example, perfusion values may be respectively expressed as colors, and delay times may be respectively expressed as concentrations of cross-hatches. Or, perfusion values may be respectively expressed as brightness of colors, and delay times may be respectively expressed by chroma of colors.

Still alternatively, the two images may be overlapped on each other, or only the perfusion image may be displayed while indicating a delay time for a portion corresponding to a position where a mouse pointer is located on the perfusion image. In the case of displaying only the perfusion image, portions causing abnormal delay times may be blinked (or indicated at maximum brightness or cross-hatched). In this manner, when an abnormal region is detected on one of the images, the abnormal region may be highlighted (by a bold frame, animation, or blinking) on the other image. Further, various display methods as described above may be switched through a GUI from the operation unit 9.

Owing to comparative display as described above, for example, risk can be found in the delay image even from regions which are observed to be normal in the perfusion image. Accordingly, it can be determined that a treatment is required. In the example of FIG. 8, a lower center part of a screen in the perfusion image seems to be properly supplied with blood and to cause no trouble while the same part in the delay image is found to cause a long perfusion delay. As a result of this, this region is found to cause no problem in supply of blood and to require a long time until a contrast medium flows into. Clinically, for example, a myocardial region where a completely obstructed blood vessel is supposed to exist, and a collateral circulation is also supposed to exist and supply a sufficient blood flow to the region. This myocardial region is not ischemic. Therefore, this region will not soon lead to death. However, the situation of blood supply from a collateral circulation is so dangerous that ischemia may soon occur if only some motion or the like causes narrowing of the collateral circulation. A treatment is therefore to be taken if possible.

In this respect, if both images are displayed arranged in a row according to the present image processing apparatus, comparative observation of both images is facilitated. Although the left image in FIG. 8 teaches that a blood flow is supplied even to a peripheral portion near the center of this image, the right image shows a highly concentrated cross-hatch in a corresponding region, which implies that angiographic imaging of this region has required a long time. This result cannot be known by a visual check of only the left image but is a symptom which can be diagnosed exactly by a display method capable of displaying two images compared with each other. Thus according to the present embodiment, not only information is merely displayed but also information which assists diagnoses of doctors can be provided.

(Modification 1)

In the step S11, the delay-time measurement unit 111 measures delay times, from time density curves at perfusion regions (myocardium) which are generated by the time-density-curve generation unit 110. In Modification 1, the delay-time measurement unit 111 measures time density curves, from time density curves at plural regions on which are generated respectively for branches of a blood vessel.

Concerning a measurement method for measuring delay times, a definition "TIMI Frame Count (TFC)" is a term which is used among a lot of cardiologists. This definition means an index which expresses a time required for a contrast medium to reach the periphery from a coronary trunk. According to the definition, one TFC is decided for each session of contrast imaging. In actual, however, branches have respectively different TFCs.

Figure 9A:
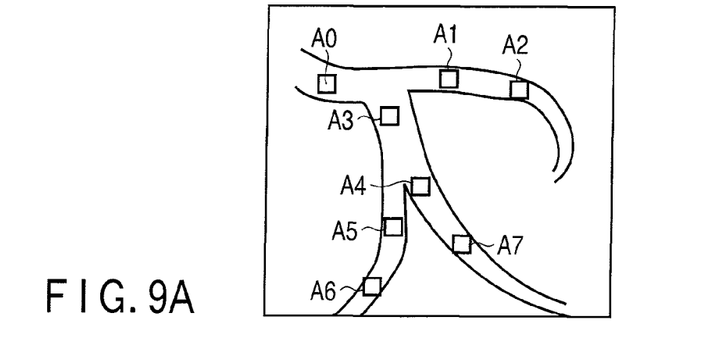
FIGS. 9A, 9B and 9C are to graphically describe a processing in Modification 1.
Figure 9B:
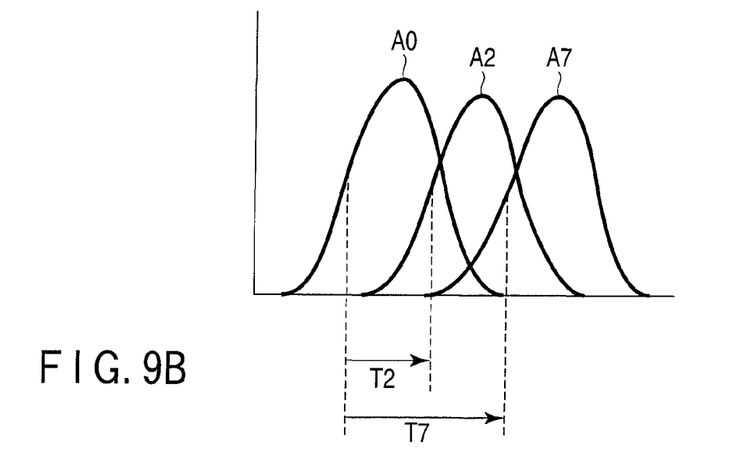
Figure 9C:
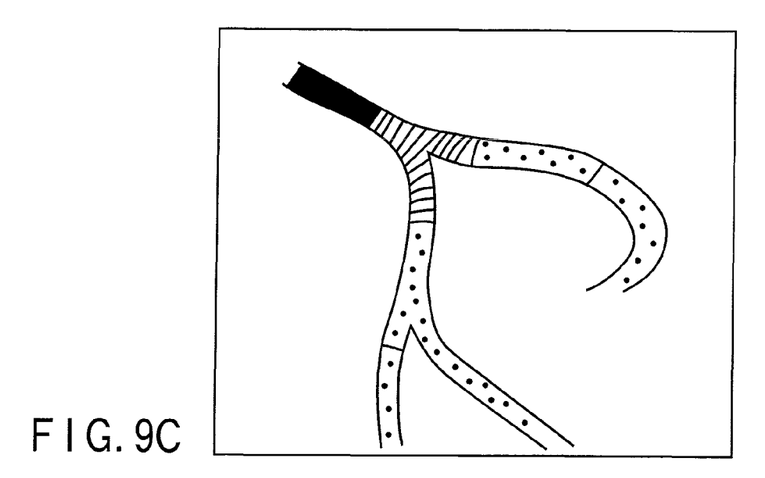
Figure 10:
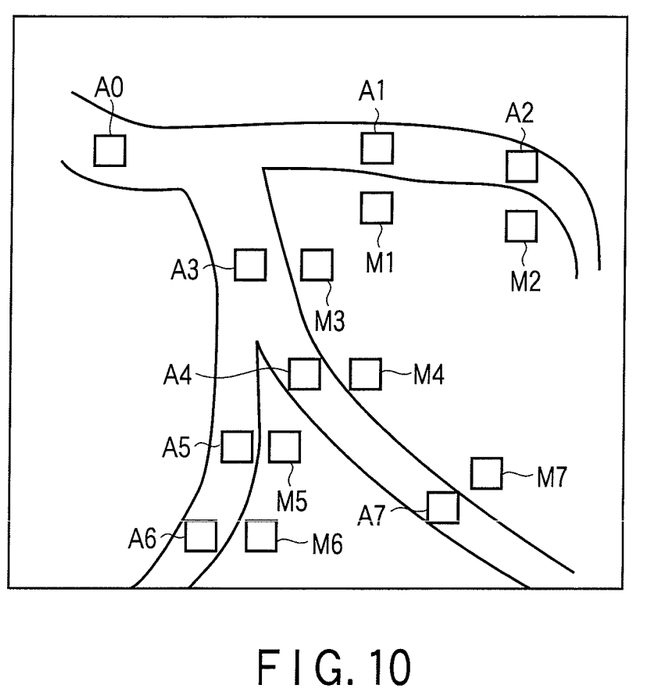
FIG. 10 is to graphically describe the processing in Modification 1.

Specifically, for example, the delay-time measurement unit 111 sets plural regions of interest (ROI) on blood vessels as represented in FIG. 9A, and defines delay times in a manner that T2 is a delay time from A0 to A2, T7 is a delay time from A0 to A7, and so on, as represented in FIG. 9B. FIG. 9C represents a delay image which is generated, for example, by expressing blood vessels to have densities which respectively differ depending on sizes of the delay times T2 and T7. FIG. 10 represents an example in which delay times for the foregoing blood vessel are adopted as delay times for nearby myocardium. Specifically, for example, a delay time T1 from A0 to A1 is taken as a delay time for a myocardium M1. In this manner, delay times for not only blood vessels but also myocardium can be obtained simultaneously.

(Modification 2)

Modification 2 proposes a method of calculating delay times so as to comply with a flow model of a contrast medium flowing into/out of myocardium, as a modification of the measurement method for measuring delay times in the step S12. Jpn. Pat. Appln. KOKAI Publication No. 2008-136800 proposes a method of calculating perfusion by using a model defined by an expression as follows.

$$\frac{dC_{myo}(t+T)}{dt} \cong K_1 C_a(t)$$

In the above expression, Cmyo(t), Ca(t), t, T, and K1 respectively denote myocardial density, blood vessel density, time, delay time, and perfusion value. To comply with the model defined by the expression, the right side of the expression need be maximized at the time t when the left side of the expression takes a maximum value. The delay-time measurement unit 111 measures an optimal delay time T for each region, from time density curves Ca(t) for blood vessels which are obtained from images, and time density curves Cmyo(t) for perfusion regions which are also obtained from images.

(Modification 3)

Modification 3 is to define a setting method for setting a zero point for delay times.

In the measurement processing for measuring delay times in the step S12, what time point should be set as the zero point for delay times or the time t=0 need be defined. In general, a device (injector) for injecting a contrast medium is provided, and an injection start signal therefrom is obtained. The injection start point is set as t=0. According to this method, however, a time lag exists from when the injector starts injecting a contrast medium to when the contrast medium is actually injected out of a tip end of a catheter.

Figure 11A:
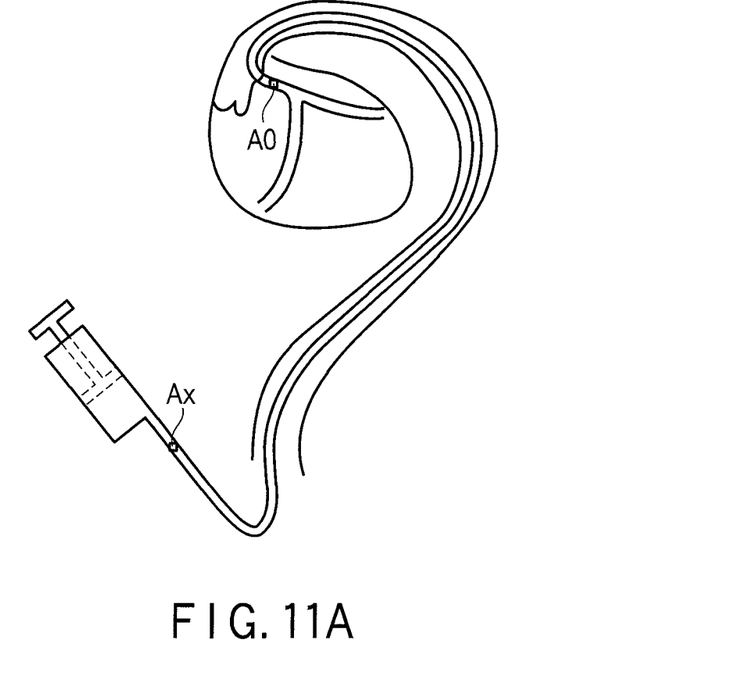
FIGS. 11A and 11B are to graphically describe a processing in Modification 3.
Figure 11B:
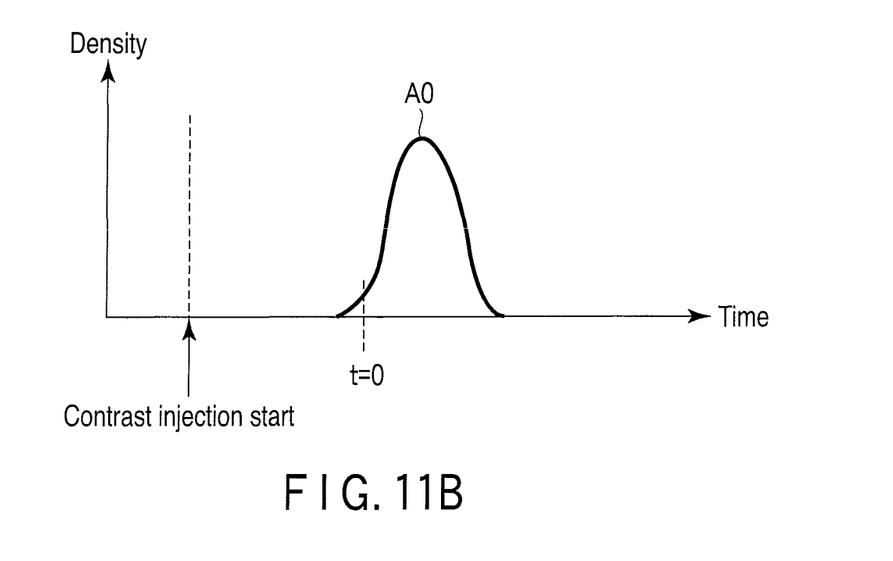

Consideration is taken into a case that ratios of delay times between before and after a treatment may be obtained as will be described later. In this case, such a time lag is not preferable. Hence, as represented in FIG. 11A, the delay-time measurement unit 111 sets a ROI at the tip end of the catheter inserted in a blood vessel of an organ or at a blood vessel existing slightly ahead of the catheter on an image. Further referring to a time density curve at the ROI, a rising point of a reference time density curve is set as the zero point for time delays, as represented in FIG. 11B.

(Modification 4)

Modification 4 is configured to be capable of dealing with an organ which moves cyclically like a heart.

Since a heart beats, time density curves become wavy if time density curves are generated by using all frames of obtained images. Therefore, the time-density-curve generation unit 110 adds a processing of, for example, averaging between frames within a predetermined period before generating time density curves in the step S12. Alternatively, as disclosed in Jpn. Pat. Appln. KOKAI Publication No. 2008-136800, the time-density-curve generation unit 110 may generate time density curves by using one image in a particular cardiac phase for each heart beat. An organ which cyclically moves requires the processing as described above, compared with an organ which does not move. Therefore, the time-density-curve generation unit 110 may be provided with a processing mode for an organ which moves cyclically, and another processing mode for an organ which does not move. These two processing modes may be selectively used depending on organs.

(Modification 5)

Modification 5 is a method for correcting delay times depending on distances to respective perfusion regions from a reference region.

Figure 12A:
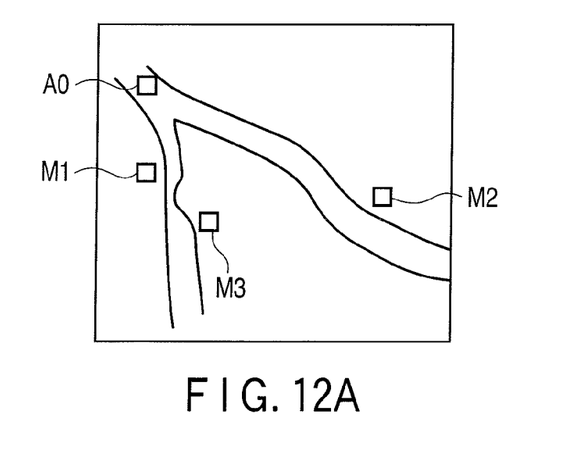
FIGS. 12A, 12B and 12C are to graphically describe a processing in Modification 5.
Figure 12B:
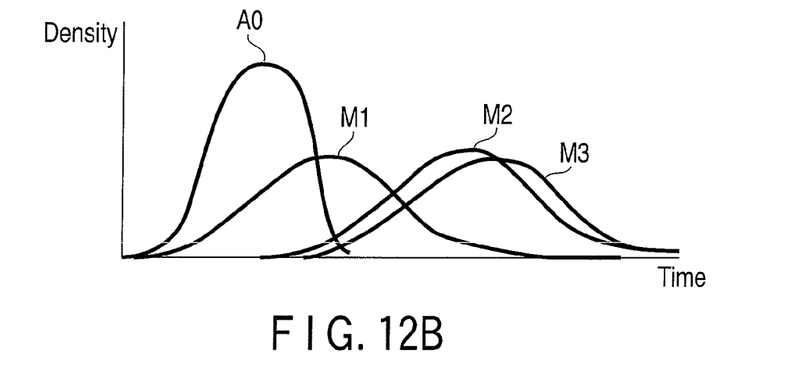
Figure 12C:
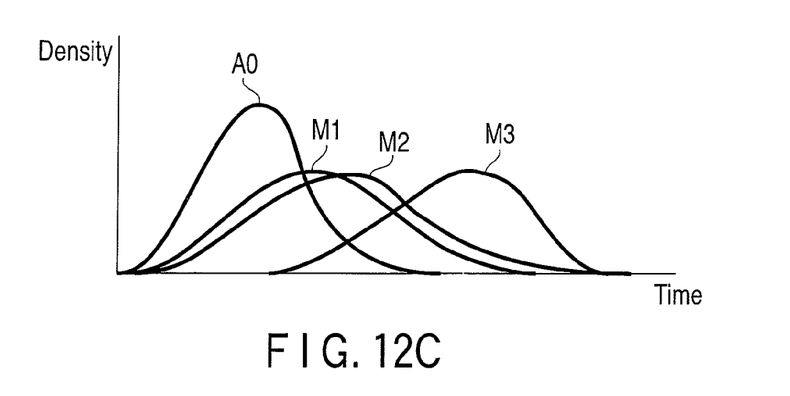

For example, in FIG. 12A, consideration will now be taken into a normal myocardial region M1, a region M2 distant from a reference region, and a region M3 existing on the periphery of a constricting lesion which obstacles a blood flow. According to a method for calculating perfusion values for a constant period without depending in the delay times, in FIG. 12B, a perfusion value only at M1 is calculated to be normal, and perfusion values for M2 and M3 are determined to be abnormal. A method to correct the delay times at myocardial regions depending on distances from a tip end A0 of a catheter (reference region) to myocardial regions is proposed in the delay-time measurement unit 111. In FIG. 12A, distances to M1 and M3 from A0 are short while a distance to M2 from A0 is long. The delay-time measurement unit 111 performs a correction for shortening delay times, depending on the distances. In this manner, the delay time for M2 is greatly shortened, and the delay time for M3 is shortened within a range being greater than M1 and smaller than M2. As a result, curves corrected as represented in FIG. 12C are obtained, and the perfusion values are determined to be normal in M1 and M2 while the perfusion value is determined to be delayed in M3.

(Modification 6)

Modification 6 is configured to display both of a perfusion image, which is generated on the basis of delay times at respective perfusion regions, and another perfusion image which is generated independently of the delay times. That is, the perfusion-image generation unit 113 generates not only a perfusion image (first image) generated through the step S13 but also another perfusion image (third image) expressing spatial distribution of perfusion values calculated by using an equal delay time for all pixels (regions). The perfusion-image generation unit 113 displays both perfusion images on the display unit 12. From the perfusion image generated independently of the delay times, perfusion amounts at a predetermined timing can be observed. However, if a perfusion delay occurs, the perfusion delay is then determined to be abnormal, and whether or not blood is supplied cannot be known. On the other side, from the other perfusion image generated on the bases of delay times for respective perfusion regions, perfusion amounts can be observed, and if a perfusion delay occurs, the perfusion delay is then determined to be normal. In this manner, characteristics of both images can be seen at a glance, and valuable information for doctors can be provided. Further, an image expressing differences between the two images can be displayed. Then, risk such as perfusion delays can be specified.

(Modification 7)

Figure 13:
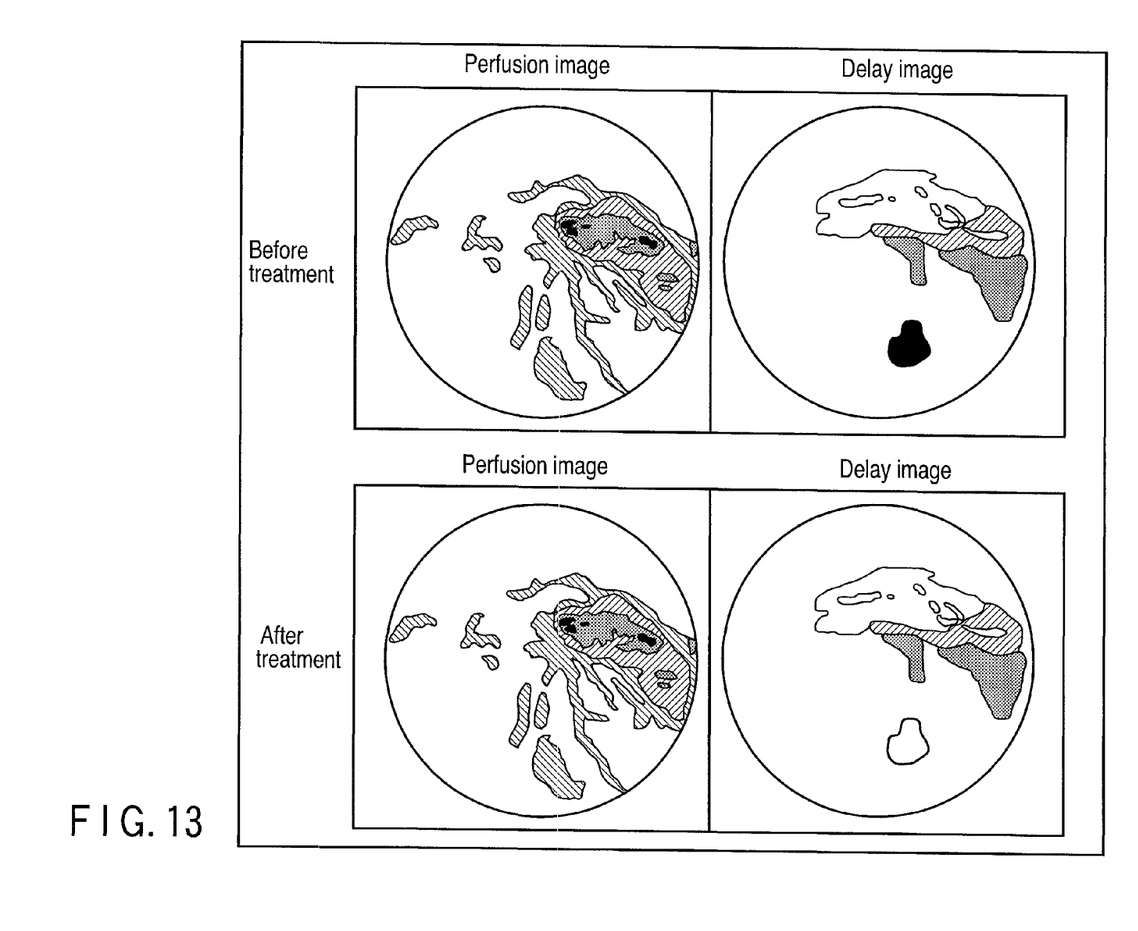
FIG. 13 represents an example of displayed images in Modification 7.

The image processing unit 11 may perform the image processing described above on data before and after a treatment, and images before and after the treatment may be displayed. For example, as represented in FIGS. 13, the perfusion-image generation unit 113 and the delay-image generation unit 114 generate total four images, e.g., a perfusion image and a delay image before a treatment, and a perfusion image and a delay image after the treatment. The perfusion-image generation unit 110 displays these images on the screen of the display unit 12, comparing the images between before and after the treatment. Perfusions seem to have not changed between before and after the treatment. However, a portion where density was high has disappeared in the image after the treatment, i.e., a delay has been eliminated obviously. This means that an operation for avoiding a "risk" as previously described has been successful.

Further, the perfusion-image generation unit 113 and the delay-image generation unit 114 may generate images which express distribution of ratios obtained by dividing perfusion values and delay times after a treatment by perfusion values and delay times before the treatment. The display unit 12 may display an image concerning ratios of the perfusion values before and after the treatment, and an image concerning ratios of the perfusion values before and after the treatment, with both images arranged on the left and right sides, respectively. Differences in perfusion value and delay time between before and after a treatment may be used in place of the ratios.

In the above embodiment, the image processing apparatus according to the invention has been described to be configured such that the image processing apparatus is integrated with an X-ray diagnostic apparatus. However, the image processing apparatus may alternatively be configured as a separate independent image processing apparatus including the image collection storage unit 10, image processing unit 11, and display unit 12.

Respective functions of the image processing apparatus according to the present embodiment can be realized by installing a program for executing corresponding processing in a computer such as a workstation and by expanding the program on a memory. At this time, the program capable of causing the computer to execute corresponding methods may be stored in a recording medium which may then be distributed, wherein the recording medium may be a magnetic disc (such as a floppy (registered trademark) disc) or a hard disc), an optical disc (such as CD-ROM or DVD), or a semiconductor memory.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
an X-ray tube which generates an X-ray;
an X-ray detector which detects the X-ray which penetrates a subject;
a storage memory which stores data of a plurality of X-ray projection images generated through a angiographic imaging sequence by the X-ray detector;
a processor configured to
generate, based on the data of the plurality of X-ray projection images, a reference time density curve concerning a reference region which is set as a blood supply region for a target portion, and a plurality of time density curves concerning a plurality of perfusion regions which are set as a blood supplied region in the target portion;
measure a plurality of delay times for the plurality of perfusion regions respectively based on relationships between the reference time density curve and the plurality of time density curves;
calculate respectively for the perfusion regions, a plurality of first indices expressing correlations of the plurality of time density curves to the reference time density curve within a period after elapse of the delay times and a plurality of second indices expressing correlations of the plurality of time density curves to the reference time density curve within a period after elapse of an equal delay time in all of the perfusion regions;
generate a first image expressing spatial distribution of the plurality of first indices in the perfusion regions and a third image expressing spatial distribution of the plurality of second indices in the perfusion regions; and
a display which displays the first image together with the third image.

2. The X-ray diagnostic apparatus according to claim 1, wherein the plurality of first indices respectively include blood flow states of the plurality of the perfusion regions.

3. The X-ray diagnostic apparatus according to claim 1, wherein the processor generates the plurality of time density curves concerning the perfusion regions on the basis of time density curves near the plurality of the perfusion regions, respectively.

4. The X-ray diagnostic apparatus according to claim 1, wherein the processor measures the plurality of delay times on the basis of a flow model of the contrast medium flowing into/out of the plurality of the perfusion regions.

5. The X-ray diagnostic apparatus according to claim 1, wherein the processor corrects the plurality of delay times, respectively depending on distances to the plurality of the perfusion regions from the reference region.

6. The X-ray diagnostic apparatus according to claim 1, wherein:
the processor generates a second image expressing spatial distribution of the plurality of delay times in the perfusion regions; and
the display displays the first image and the second image arrayed in parallel.

* * * * *